United States Patent [19]

Anderson et al.

[11] Patent Number: 4,818,883

[45] Date of Patent: Apr. 4, 1989

[54] LUMINOMETER APPARATUS

[75] Inventors: Joseph C. Anderson; Martin Applebaum, both of London, England

[73] Assignee: Biolite Ltd., London, England

[21] Appl. No.: 133,569

[22] Filed: Dec. 16, 1987

[30] Foreign Application Priority Data

Dec. 17, 1986 [GB] United Kingdom ............... 8630136

[51] Int. Cl.⁴ .......................................... G01N 21/76
[52] U.S. Cl. .............................. 250/361 C; 250/458.1; 250/459.1; 422/52; 436/172
[58] Field of Search ................. 307/351; 328/115; 250/458.1, 459.1, 361 C; 436/172; 422/52; 356/317, 318, 417

[56] References Cited

U.S. PATENT DOCUMENTS 4,438,329  3/1984  Ford et al. ................. 250/459.1
4,581,922  4/1986  Aiello ......................... 307/351

FOREIGN PATENT DOCUMENTS 2089971  6/1982  United Kingdom ........... 250/458.1

OTHER PUBLICATIONS

Zyat'kov et al., "Device for Analyzing the Spectral Composition of Weak Luminous Fluxes", Zhurnal Prikladno; Spektoskopii, 22(3), pp. 482–486, Mar. 1975.

Hazan et al., "An Improvement of Nanosecond Fluorimeters to Overcome Drift Problems", Rev. Sci. Instrum., 45(12), Dec. 1974, pp. 1602–1604.

Primary Examiner—Carolyn E. Fields
Attorney, Agent, or Firm—Ladas & Parry

[57] ABSTRACT

A luminometer apparatus has a light-tight box (12) into which a cuvette (2) containing a sample and a reagent are located for producing a phosphorescent reaction. The phosphorescent reaction is detected by a photodetector (PD) and a shutter (3) is interposed between the cuvette and the shutter. Output signals from the photodetector are applied to a circuit arrangement (FIG. 4) which detects the phosphorescent reaction at predetermined intervals and by subtracting the successive values of light from one another so a measured peak value of light intensity is determined. The shutter is closed and the dark current signal of the photodetector is determined and subtracted from the measured peak value. A true peak intensity of the emitted light is thus derived and the concentration of the material being assayed is calculated by raising the peak intensity to the power n where n has a value between 0 and 9 predeterminedly derived for the sample.

11 Claims, 4 Drawing Sheets

LUMINOMETER APPARATUS

This invention relates to a luminometer apparatus for determining the peak intensity of light emitted as a result of a phosphorescent reaction, particularly although not exclusively a chemiluminescent or bioluminescent reaction.

A known luminometer is the Lumac Luminometer Model 1070 which has an aperture for accepting a cuvette into which a sample is placed and a reagent is injected into the sample to produce a luminescent output. The luminescent output normally increases to a peak and then decreases. In the prior art luminometer the instrument zeroes the dark current of a silicon photodiode detector prior to injection of the reagent. The apparatus after injection of the reagent is arranged to either detect the light emitted at predetermined intervals of time or integrates the emitted light over a predetermined time interval of ten or forty seconds.

The disadvantage with the known luminometer is that neither method of measurement is capable of detecting the peak light output and additionally by zeroing the photodiode dark current prior to making a measurement it is possible for the dark current to drift due to temperature variation over the time taken for the measurement.

It is an object of the present invention to at least partially mitigate the foregoing disadvantages.

According to one aspect of this invention there is provided a luminometer apparatus including circuit means having a photodetector arranged to detect light emission from a phosphorescent reaction exhibiting a peak light value, said circuit means being arranged to produce a signal indicative of the intensity of the peak light value.

Preferably the circuit means includes means arranged to sample the light emission from the phosphorescent reaction at predetermined time intervals and by subtracting consecutive said samples to determine the peak light value, means arranged to detect the dark current signal of the photodetector and means for subtracting said dark current signal from said peak light value.

In an embodiment of this invention the phosphorescent reaction is created by reacting a reagent with a sample and there is provided a microprocessor arranged to determine the concentration of the sample by calculating $I^n$, where I is the peak light value and n is a variable between 0 and 9, and input means arranged to input n to the microprocessor.

So as to obtain the required light values conveniently a shutter means is located between the photodetector and the phosphorescent reaction whereby when the shutter is open the photodetector detects light from the reaction and when the shutter is closed the photodetector dark current is determinable.

Advantageously a display is provided arranged to display the output of the microprocessor which is one of the detected light emission from the photodetector, the photodetector dark current, the concentration of the sample, the value of the concentration with respect to a predetermined value.

Conveniently the shutter is an electromechanical shutter comprising a motor driven rotatable member with an aperture therein.

According to another aspect of the invention there is provided a method of determining the peak light value of a phosphorescent reaction by the steps of detecting the light signal output from the phosphorescent reaction at predetermined time intervals, subtracting successive light output readings from one another whereby the peak signal is determinable. Conveniently said predetermined time intervals are 5 seconds.

Preferably the peak signal is determined by a photodetector and associated circuit means and when the peak signal has been determined the photodetector dark current is measured and subtracted from the peak signal measurement.

Advantageously a phosphorescent reaction is created by reacting a reagent with a sample and a microprocessor is arranged to determine the concentration of the sample by calculating $I^n$ where I is the peak light value and n is a variable value between 0 and 9 which is inputted to the processor whereby the concentration of the sample is evaluated by the microprocessor after the dark current signal has been subtracted from the measured peak light signal.

An embodiment of the invention will now be described by way of example, with reference to the accompanying drawings, in which.

The invention will be particularly described with reference to determining the degree of fermentation of wine although it is to be understood the use of the apparatus is not limited to such a use.

It is known that malic acid is normally present in wine and the amount of malic acid in the wine is a measure of the malo-lactic fermentation such that when malic acid is present below a standard value fermentation is taken to be complete. Thus by reacting wine with immobilised enzymes including luciferase and cofactors in combination the malic acid reacts with the enzymes and light is emitted. The quantity of light that is emitted is a measure of the amount of malic acid present in the wine. The intensity of light is a power law so that if light intensity is plotted on a logarithmic scale as an ordinate against an abscisse of a logarithmic concentration of malic acid in milligrams per litre a straight line is produced, the slope of which is a factor n (typically in the range 2 to 2.5) in an equation $C = AI^n$ where C is concentration of the material being assayed, A is a preset constant (effectively a sensitivity control) and I is the peak intensity of the emitted light. For different wines the factor n is generally constant but the value A does vary according to the activity of the enzyme preparation. In the present example where fermentation of wine is to be measured, a batch of cuvettes are prepared in a laboratory having a solution with a known quantity of malic acid and the solution is reacted with immobilised enzymes, and cofactors to determine the values n and A. The immobilised enzymes and cofactors are in a cuvette and are sold with the thus determined values of n and A given to the user for the cuvette. Thus in use, the value of A and n for any particular batch of cuvettes is determined in the laboratory and the user relies on these values when using the apparatus.

Figure 1:
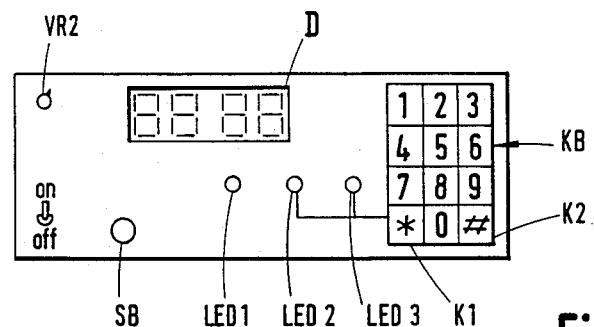
FIG. 1 is a view of the front panel of the luminometer apparatus in accordance with this invention.

Referring now to FIG. 1, the front panel is provided with a four digit alpha-numeric display D which display readings of light intensity derived from a phosphorescent reaction which may be bioluminescent or chemiluminescent in nature. The peak intensity (I) in the preferred embodiment of this is the measured peak intensity of the reaction less the dark current of a silicon photodiode photodetector used to detect the reaction. A calibrated gain control VR2 enables the user to set the appropriate value of A such that the display reading represents, for example, milligrams per litre, and a keyboard KB enables the user to set the appropriate value of n.

Keyboard KB also has a key K1 which, when pressed, closes a shutter (if the shutter was originally open) or opens the shutter (if the shutter was originally closed) causing the display D to show either the light current or the dark current at will. A light emitting diode LED2 indicates when the shutter is open and light emitting diode LED3 indicates when the shutter is closed. Key K2 is an entry key for n and must be pressed before the value of n can be inserted by a user on the keyboard KB. The value of n is in the range of 0 to 9 but for wine fermentation is 2.5. The apparatus also has a start button SB which causes the apparatus to begin an automatic measurement cycle. At the start of the cycle the display shows SOSO for shutter open. When the peak reading is detected the shutter closes and the display shows SCSC for shutter closed, for a period sufficiently long (typically 20 secs) for the true dark current to be measured. After this period the display shows the difference between the light and dark currents. The instrument is battery powdered and a light emitting diode LED1 indicates when the batteries need replacing.

Figure 2:
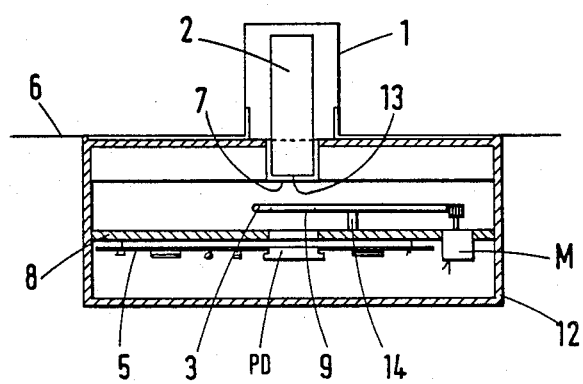
FIG. 2 is a diagrammatic cross-section of the optical system and shutter mechanism of the apparatus.
Figure 3:
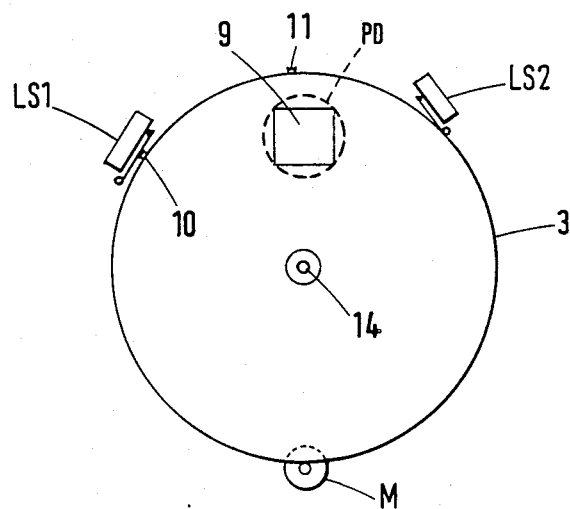
FIG. 3 is a diagrammatic plan view of the shutter shown in FIG. 2.

Referring now to FIGS. 2 and 3, a light-tight box 12 is mounted within a casing 6 of the apparatus and is enclosed by a removable cap 1 which fits onto the exterior of the casing 6. A sample to be analysed is introduced into a cuvette 2 which is supported by a glass window 7. The cuvette has a transparent base 13 of area 1 cm$^2$ and light generated by the phosphorescent, bioluminescent or chemiluminescent reaction within the cuvette is detected by a photodetector PD. A circular shutter 3 is interposed between base 13 of the cuvette 2 and the photodetector PD and is rotatably driven about its mounting shaft 14 by a motor M acting upon the shutter circumference. A square aperture 9 (as best seen in FIG. 3) is formed in shutter 3 and the shutter is rotationally oscillated by motor M between normally closed limit switches LS1 and LS2 actuated to open by stops 10, 11 respectively on the shutter circumference to cause the aperture 9 to move into and out of register with the base 13 and photodetector PD. The limit switches LS1, LS2 may be mechanical switches or reed relays. As shown in FIG. 2, motor M is mounted upon a support 8 which also carries a circuit board 5 on which the photodetector PD and its preamplifier circuit is located.

Figure 4:
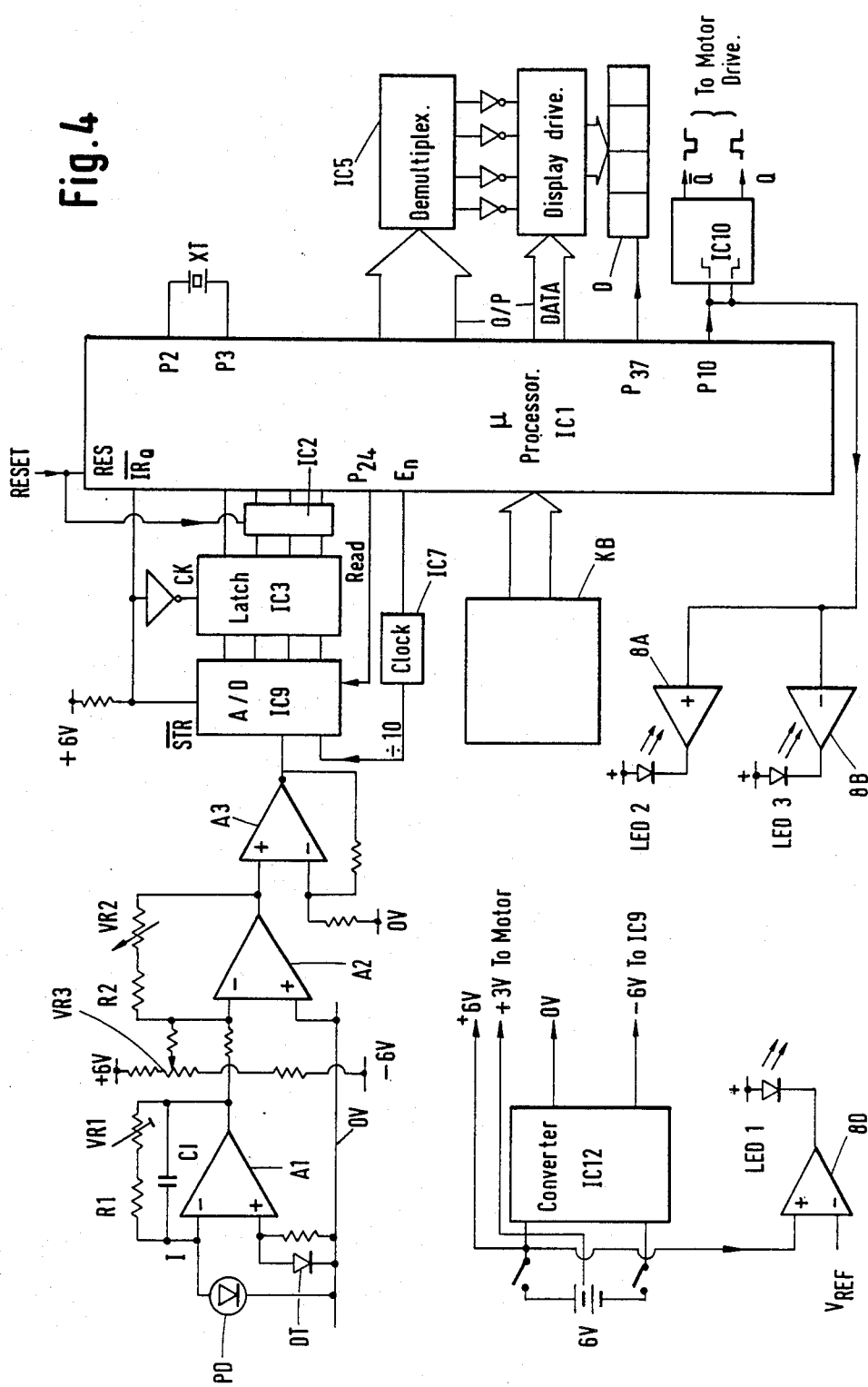
FIG. 4 is a block diagram showing the control circuitry of the apparatus.

The system shown in FIG. 4 is controlled by a microprocessor IC1 which is suitably a Hitachi HD63701-VOP programmed microprocessor. This is programmed to take digital samples of the output from photodiode PD at predetermined intervals of say 5 seconds. The software which implements control during the measurement cycle is described below with reference to FIG. 6.

The output from photodiode PD (which operates in the photovoltaic mode) is fed to a sixteen-bit analogue-to-digital converter IC9 via a chain of three operational amplifiers A1, A2, and A3. So as to provide temperature compensation for the photodiode PD a diode DT having a similar temperature sensitivity to the photodiode is used to provide a reference input to the non inverting input of the operational amplifier A1 with the photodiode being connected to the inverting input thereof. Operational amplifier A1 acts as a current/voltage converter with a transfer impedance of IM ohm; operational amplifier A2 is an inverting amplifier with a gain of between 10 and 100 which is controlled by the potentiometer VR2 on the front panel, and operational amplifier A3 provides a fixed gain of x10. The feedback loop R2, VR2 of amplifier A2 incorporates a preset potentiometer VR3 which is set so as to give a reading on the display of zero when the shutter is closed over photodiode PD to offset the photodiode dark current at room temperature. Operational amplifier A1 also incorporates a parallel connected capacitor C1 in its feedback loop across resistor R1 and potentiometer VR1 to help mitigate the effect of high frequency noise or other interference upon successive light intensity readings and the time constant in the present embodiment is approximately 2.5 seconds.

Analogue-to-digital converter IC9, receiving output from amplifier A3, is a four-digit B.C.D. (binary coded decimal) converter and feeds a latching chip IC3 which consists of four D-type flip flops acting as a memory interface receiving 16 bit data and outputting 4 bit data. When the four inputs to latch IC3 from A/D converter IC9 have each received four bits the latched data is fed to IC1 under the control of a handshake routine which involves feeding signals to the interrupt request line $\overline{IR}_q$ and the clock input CK of IC3 via an inverter from the strobe $\overline{STR}$ O/P of A/D converter IC9. Thus, the interrupter request line $\overline{IR}_q$ of microprocessor IC1 is energised each time a decade of data has arrived in latch IC3. During this process, a data selector IC2 simply presents decades data to the microprocessor IC1. However, IC2 is also utilised to set the microprocessor IC1 in the correct operating mode when a RESET signal is applied. This RESET signal is generated in response to the pressing of push button SB (FIG. 1). A clock IC7 controlled by a 4 MHz crystal XT provides a divide by 10 clocking signal to A/D converter IC9. The sampling sequence described above is initiated by a READ signal to A/D converter IC9 from pin P$_{24}$ of microprocessor IC1. This READ signal, which determines the sampling interval, is generated in accordance with software programmed into an EPROM of the microprocessor IC1 and is described below with reference to FIG. 6.

The digital sampling of light intensity described above is initiated and terminated in synchronism with control of the shutter by means of a monostable IC10 which generates square wave pulses on the rising and falling edges of its inputs from port line (P$_{10}$) of microprocessor IC1. As will subsequently be described with reference to FIG. 5, these inputs cause the motor M to rotate shutter 3 to cover and uncover the photodetector PD. P$_{10}$ of microprocessor IC1 also feeds two comparators 8A and 8B which drive LED2 and LED3, to indicate the shutter open and shutter closed states respectively.

The four decade light intensity data derived from A/D converter IC9 and latch IC3 is processed in conjunction with the value of n feed into microprocessor IC1 from keyboard KB to determine the peak light intensity. After making a correction to allow for the measured dark current from photodetector PD, the resulting data (which represents the concentration of the analyte) is output from an eight bit output port O/P in multiplexed form. This multiplexed output is applied to a digit select de-multiplexer IC5 whose four bit data bus output is applied via inverters to display drive IC6 to direct the four bit data to the appropriate digits of LCD display D.

Power for the system is provided by four 1.5 volt cells which are connected to produce +6 volts for the electric system rail potential and +3 volts for the motor. A −6 volt level for A/D converter IC9 is derived from the +6 volt rail by a voltage converter IC12, a two gang on/off switch being interposed between the cells and converter IC12. A diode stabiliser (not shown) derives a signal $V_{REF}$ from the cells which is applied to a comparator 8D which samples the cells voltage to give a battery state indication via LED1.

Figure 5:
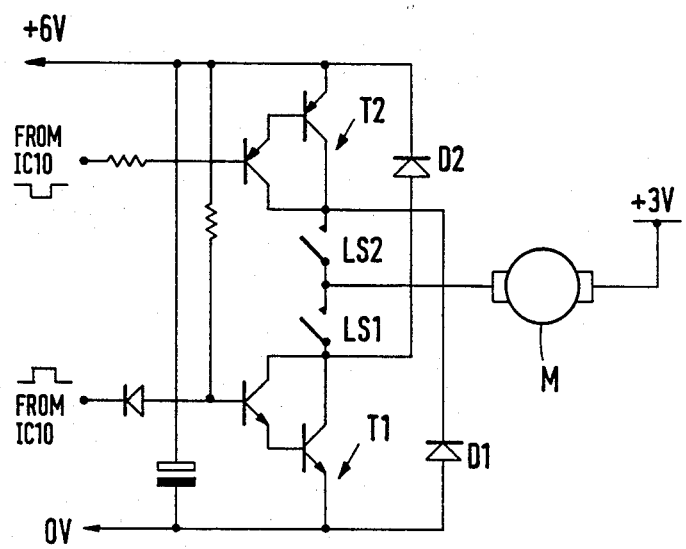
FIG. 5 is a circuit diagram of the motor control drive circuitry.

The drive circuitry for motor M is shown in FIG. 5. One terminal of the motor is connected to the +3 volts rail and the other is connected either to the +6 volt rail or to 0 volts according to whether Darlington power transistor T2 or Darlington power transistor T1 is switched on. These transistors are switched by the output pulses $\overline{Q}$ and Q respectively from IC10 (FIG. 4) which are generated in dependence upon the routine stored in microprocessor IC1. Limit switches LS2 and LS1 are normally closed but are opened if the shutter rotates beyond predetermined limits and so act as a fail-saft mechanism in the event T1 or T2 are inappropriately switched. The circuit incorporates protective diodes D1 and D2.

Figure 6:
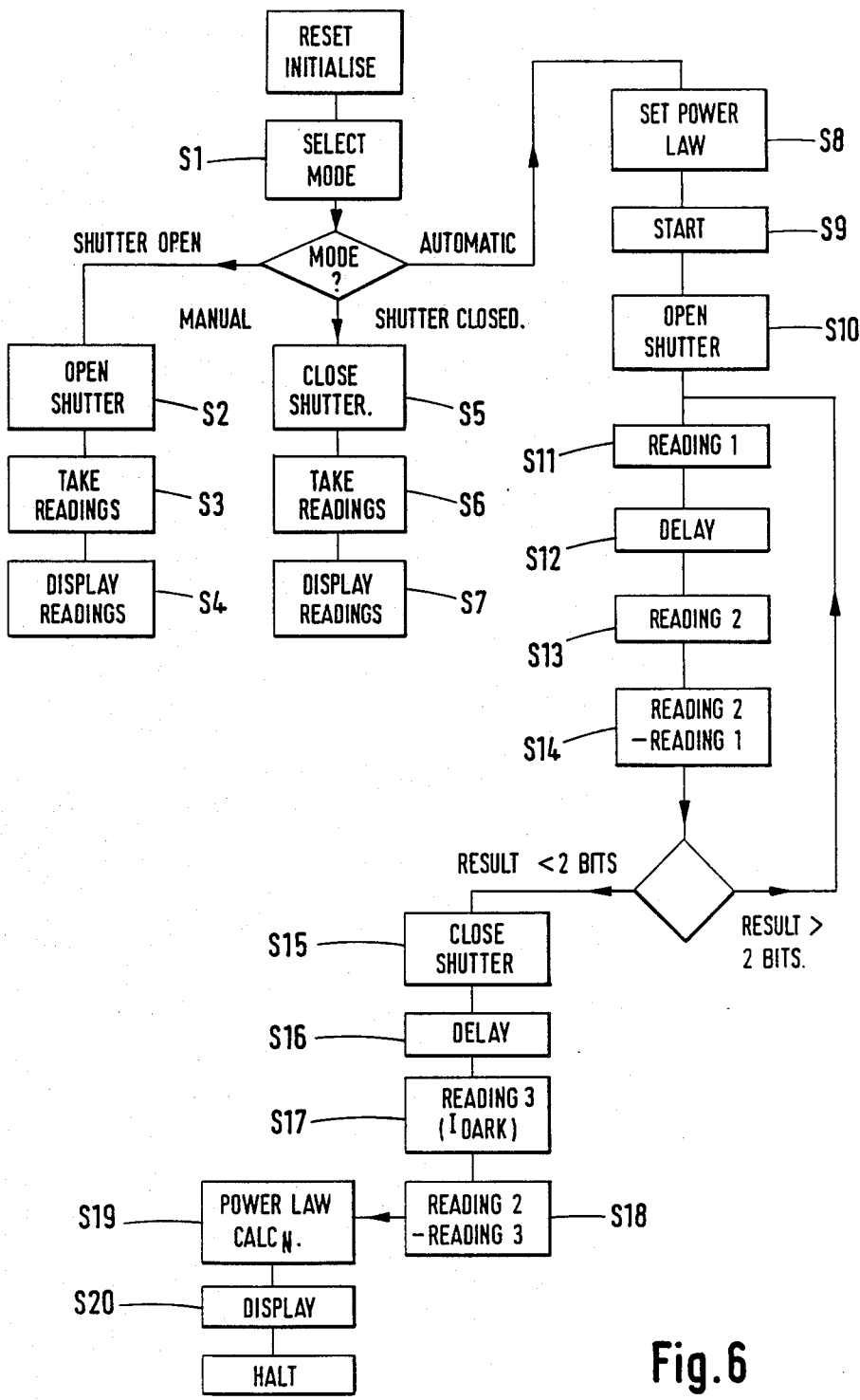
FIG. 6 is a flow chart showing the operation of the apparatus.

The overall operation of the system will now be described with reference to FIG. 6, which is a flow diagram of the routine stored in microprocessor IC1, and also with reference to the front panel illustrated in FIG. 1.

A sample is introduced into a cuvette in which immobilised reactants are present, the cuvette is shaken to commence the phosphorescent reaction and the cuvette is placed inside the box 12.

After switching the apparatus on, the key K1 is depressed to ensure that the shutter is closed and the shutter closed light emitting diode LED3 is illuminated. The gain control VR2 is adjusted to a figure for A predeterminedly derived for the particular assay being performed. The lid of the light-tight box is removed and the cuvette 2 is placed in the box and the lid is carefully placed to ensure that no light is able to enter the box. The shutter 3 is opened by depressing key K1, light emitting diode LEd2 is illuminated and the display registers a value corresponding to the light emitted from the sample. This procedure confirms that the instrument is working.

For automatic measurements Key K2 is depressed and the display will indicate CA 1.0 and the required power law for n is inserted by depressing the appropriate numerical keys. The power law n is predeterminedly derived for the reactant contained in the cuvette when it is produced in the laboratory as described above. The numbers required for the power law are entered in the display from right to left so that if the "2" key is pressed a "2" will appear in the right hand window of the display. If this is followed by pressing the "5" key, the "2" will move one place left and the "5" will appear in the right hand window of the display. The display D will then show CA 2.5 and the power law inserted is thus 2.5. The step of setting the power law is step S8 in FIG. 6. The start button SB is then pressed (step S9). This causes the apparatus to begin a measurement cycle. The display D indicates SOSO (shutter open) which is step S10 in FIG. 6. A first reading is taken (step S11), a five second delay occurs (step S12) and then a further reading is taken (step S13). The reading taken in step S13 is subtracted from the reading taken in step S11 (step S14) and if the difference is greater than two bits (one digit in the last numeral of the display) the steps S11 to S14 are repeated. When the difference becomes less than two bits the shutter is closed (step S15) and the display D reads SCSC. After a twenty second delay (step S16) a third reading is taken (step S17) to determine the dark current. A period of twenty seconds delay is chosen as a compromise between providing sufficient time for the output of the photodetector PD output to decay and to avoid excessive drift in the dark current due, for example, to temperature changes. The dark current measurement is subtracted from the reading at step S13 in step S18 and if the dark current is equal or greater than the last reading, the display shows "BAD 1". If the light signal produced at step S13 is below a threshold value, the display reads "BAD 2". If the light signal at S13 is so high as to saturate the amplifier the display shows "BAD 3". Assuming that none of these diagnostic warnings is given, the light intensity derived in step S18 is inserted into the equation $C=AI^n$ and the concentration C is calculated (step S19) and displayed by the display (step S20) in mg/litre.

It will therefore be understood that the luminometer apparatus of the present invention is able to provide an accurate reading of the concentration of a material being assayed and that the apparatus has flexibility in that a user is able to select the gain A according to the analyte and the power law factor n is also selectable.

In the manual mode, it is assumed in the particular embodiment described that the power law is not to be set and in this mode the cuvette containing reagent and sample is placed into the apparatus and the shutter opened at step S2 by pressing key K1 (step S2), the reading is taken and displayed (steps S3, S4) and the shutter is then closed by again pressing key K1 (step S5) and readings taken and displayed (steps S6, S7). The reading displayed at step S7 may be subtracted from the display reading at step S4 so that the photodiode dark current is deducted. The manual mode of operation may be used where an instantaneous phosphorescent (bioluminescent or chemiluminescent) reaction is to be measured.

It should be noted that although the circuit shown in FIG. 4 utilises a programmed microprocessor (a Hitachi 6301 integrated circuit), other microprocessors can be used. The following are suitable numbers for the integrated circuits shown in FIG. 4:

IC2-4053, IC3-4076, IC5-LM 138, IC5-7211, IC7-4518, IC9-7135, IC10-4538, IC12-ICL 7660, A1-ICL 7650, A2-ICL 7650, and A3-OP07.

It will be apparent, however, to the man skiled in the art that other suitable integrated circuits are available.

Although the shutter 3 is shown in the above embodiment as an electro-mechanical shutter, it will be realised that an electro-optical shutter may alternatively be used.

In another embodiment of the invention a predetermined, required value of concentration is inputted and the display is arranged to produce, for example, a red light above said predetermined value, a green light below said predetermined value and an amber light on said predetermined value.

We claim:

1. A luminometer apparatus including circuit means comprising a photodetector arranged to detect light emission from a phosphorescent reaction exhibiting a peak light value, means for predeterminedly shielding said photodetector from light, means arranged to sample the light emission from the phosphorescent reaction detected by the photodetector at predetermined time intervals when the shielding means is not shielding the photodetector, subtracting means connected to said sample means for subtracting the sampled light emission of consecutive samples and for determining the peak light value, means for moving the shielding means to shield said photodetector so as to detect the dark current of the photodetector after the peak light value has been determined and said subtracting means operable for subtracting the dark current from said peak light value to determine a true intensity of the peak light value.

2. An apparatus as claimed in claim 1, wherein there is provided (a) a microprocessor for determining the concentration of an analyte which is reacted with a reagent, said microprocessor calculating $I^n$, where I is the true peak light value and n is a variable between 0 and 9, and (b) input means for inputting n to the microprocessor.

3. An apparatus as claimed in claim 2, wherein a display is provided arranged to display the output of the microprocessor which is one of the detected light emission from the photodetector, the photodetector dark current, the concentration of the sample, the value of the concentration with respect to a predetermined value.

4. An apparatus as claimed in claim 3, wherein the shutter is an electromechanical shutter comprising a motor driven rotatable member with an aperture therein.

5. An apparatus as claimed in claim 1, wherein a phosphorescent reaction container is provided and said shielding means is a shutter located between the photodetector and the phosphorescent reaction container wherein when the shutter is open the photodetector detects light from the reaction and when the shutter is closed the photodetector dark current is determinable.

6. A luminometer apparatus including circuit means comprising a photodetector arranged to detect light emission from a phosphorescent reaction exhibiting a peak light value, means for predeterminedly shielding said photodetector from light, means arranged to sample the light emission from the phosphorescent reaction detected by the photodetector at predetermined time intervals when the shielding means is not shielding the photodetector, subtracting means connected to said sample means for subtracting the sampled light emission of consecutive samples and for determining the peak light value, means for moving the shielding means to shield the photodetector so as to detect the dark current of the photodetector after the peak light value has been reached, said subtracting means operable for subtracting the dark current from said peak light value, a microprocessor for determining the concentration of an analyte which is reacted with a reagent, said microprocessor calculating $I^n$, where I is the true peak light value and n is a variable between 0 and 9, and input means for inputting n to the microprocessor.

7. A method of determining the peak light value of a phosphorescent reaction by the steps of using a photodetector to detect the light signal output from the phosphorescent reaction at predetermined time intervals, subtracting successive light output signals from one another, determining when the difference between successive light output readings falls below a predetermined minimum value to thereby determine the peak signal, determining the signal produced by the photodetector when no light falls thereon, and subtracting said produced signal from the peak signal to derive the true intensity of the peak light value.

8. A method as claimed in claim 1, wherein said predetermined time intervals are 5 seconds.

9. A method as claimed in claim 8, wherein the signal produced when no light falls on the photodetector is the photodetector dark current.

10. A method as claimed in claim 9, wherein a phosphorescent reaction is arranged to determine the concentration of an analyte by calculating $I^n$ where I is the peak light value and n is a variable value between 0 and 9 which is inputted to a microrpocessor wherein the concentration of the analyte is evaluated by the micrprocessor after the dark current signal has been subtracted from the measured peak light signal.

11. A method of determining the peak light value of a phosphorescent reaction by the steps of using a photodetector to detect the light signal output from the phosphorescent reaction at predetermined time intervals, subtracting successive light output signals from one another, determining when the difference between successive light output readings falls below a predetermined minimum value to thereby determine the peak signal, determining the signal produced by the photodetector when no light falls thereon, subtracting said produced signal from the peak signal to derive the true intensity of the peak light value, and determining the concentration of an analyte which is reacted with a reagent by calculating $I^n$ where I is the true peak light value and n is an inputted value between 0 and 9.

* * * * *